United States Patent [19]

Hofmann et al.

[11] 3,985,754

[45] Oct. 12, 1976

[54] PARA-FLUOROBENZOYLPROPYL-N-HETEROCYCLIC SUBSTITUTED QUATERNARY SALTS

[75] Inventors: Corris Mabelle Hofmann, Ho-Ho-Kus; Sidney Robert Safir, River Edge, both of N.J.

[73] Assignee: American Cyanamid Company, Stamford, Conn.

[22] Filed: May 8, 1975

[21] Appl. No.: 575,845

[52] U.S. Cl. ............ 260/294.8 D; 260/295 R; 260/297 R; 260/296 R; 424/263
[51] Int. Cl.² ............ C07D 247/00; C07D 277/38; C07D 271/06; C07D 269/00
[58] Field of Search ............ 260/294.8 D, 296 R

[56] References Cited
UNITED STATES PATENTS

| | | | |
|---|---|---|---|
| 3,511,848 | 5/1970 | Bauer et al. | 260/296 R |
| 3,551,436 | 12/1970 | Bauer et al. | 260/294.8 D |

*Primary Examiner*—Alan L. Rotman
*Attorney, Agent, or Firm*—Denis A. Polyn

[57] ABSTRACT

1-*p*-fluorobenzoylpropyl-N-heterocyclic substituted quaternary salts useful as intermediates in the preparation of novel para-fluorophenyl-N-heterocyclic substituted butanes having neuroleptic and analgesic activity.

10 Claims, No Drawings

PARA-FLUOROBENZOYLPROPYL-N-HETEROCYCLIC SUBSTITUTED QUATERNARY SALTS

BACKGROUND OF THE INVENTION

This invention resides in the field of p-fluorobenzoylpropyl-N-heterocyclic substituted quaternary salts useful as intermediates in the preparation of 1-p-fluorophenyl-4-N-heterocyclic-1-butanols, 1-p-fluorophenyl-4-N-heterocyclic-1-butanol esters and p-fluoro-γ-heterocyclic butyrophenones having neuroleptic and analgesic activity. The butanols, butanol esters and butyrophenones form the subject matter of our concurrently filed and co-pending application Ser. No. 575,846, filed May 8, 1975, incorporated herein by reference.

SUMMARY OF THE INVENTION

This invention is concerned with para-fluorobenzoylpropyl-N-heterocyclic substituted quaternary salts of the formula:

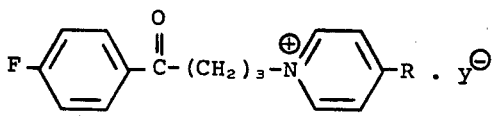

where R is ,

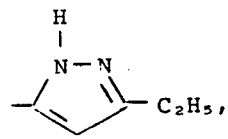 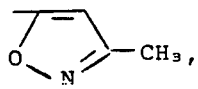

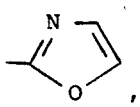 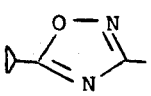

and 

and y is the anion of an acid capable of forming the quaternary salt.

This invention is also concerned with a method of preparation of the quaternary salts herein which comprises reacting a haloparafluorobutyrophenone of the formula:

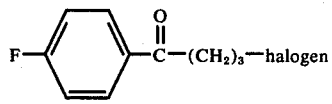

with a 4-heterocyclic pyridine of the formula:

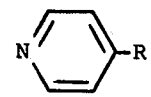

followed by treatment with a quaternizing acid to obtain a quaternary salt of the formula:

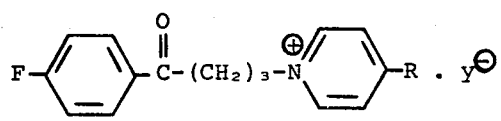

wherein R and y are as defined above and halogen is chloro, bromo and iodo.

Typical novel quaternary salts of this invention include, for example, 4-(5-cyclopropyl-3-isoxazolyl)-1-(3-p-fluorobenzoylpropyl)pyridinium perchlorate; 4-(3-ethyl-5-pyrazolyl)-1-(3-p-fluorobenzoylpropyl)-pyridinium perchlorate; 4-(5-chloropropyl-1,2,4-oxadiazol-3-yl)-1-[3-(p-fluorobenzoyl)propyl]-pyridinium perchlorate; 1-(3-p-fluorobenzoylpropyl)-

4-(4-methyl-2-thiazolyl)pyridinium chloride; 1-(3-p-fluorobenzoylpropyl)-4-(3-methyl-5-isoxazolyl)-pyridinium perchlorate; 4-(5-cyclopropyl-1,3,4-oxadiazol-2-yl)-1-(3-p-fluorobenzoylpropyl)-pyridinium perchlorate; 1-(3-p-fluorobenzoylpropyl)-3-(4-methyl-2-thiazolyl)pyridinium perchlorate; 4-acetoacetyl-1-(3-p-fluorobenzoylpropyl)pyridinium chloride; 1-(3-p-fluorobenzoylpropyl)-4-[5-(trifluoromethyl)-3-isoxazolyl]pyridinium perchlorate; and 1-(3-p-fluorobenzoylpropyl)-4-(2-oxazolyl)-pyridinium perchlorate. Representative acids which form quaternary salts are known in the art.

DETAILED DESCRIPTION OF THE INVENTION

The quaternary salts of the present invention may be prepared as follows, wherein R and y are as defined hereinabove:

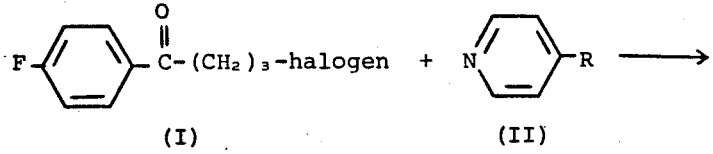

(I)            (II)

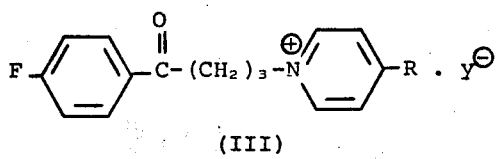

(III)

in which (I) and (II) are heated together at about 80°–100° C. for about 18–24 hours. Ether or other appropriate solvent is added and the solid which separates is collected and dissolved in water. An acid such as perchloric acid, picric acid or chloroplatinic acid is added causing precipitation of the quaternary salt (III).

The utility of the novel quaternary salts of this invention in the preparation of the central nervous system active butanols, butanol esters and butyrophenones described in Ser. No. 575,846, filed May 8, 1975, is illustrated by the following steps.

In the first step, the quaternary salt (III) of step 1 is dissolved in an alcoholic solvent, for example, methanol and sodium borohydride is added. After stirring for about 1–15 hours at about 25°–35° C., the solution is poured into water, and the unsaturated butanol (IV) which precipitates can be recrystallized from a suitable solvent such as acetonitrile, methanol or ethanol.

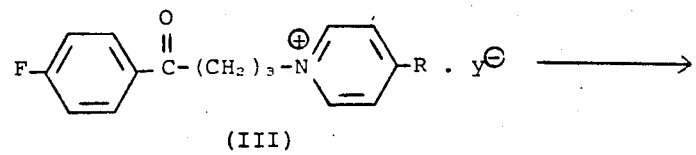

(III)

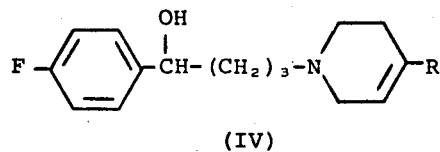

(IV)

In the second step, the unsaturated butanol (IV) from step 1 is dissolved in acetic acid and a solution of chromic acid in acetic acid is added at 25°–300° C. After stirring for about 18–24 hours the solution is poured into water and neutralized with a base such as potassium carbonate. The butyrophenone (V) is extracted from the mixture with ether and recrystallized from a suitable solvent such as ethanol.

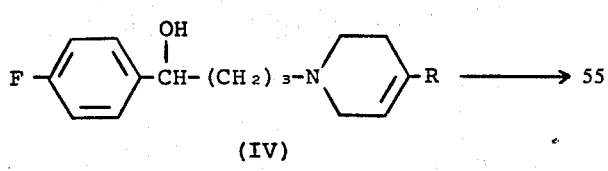

(IV)

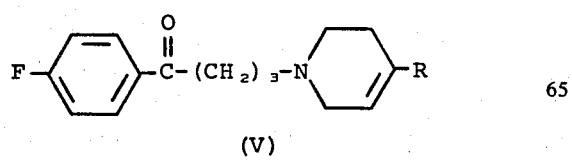

(V)

In the third step, the saturated butanol (VI) may be prepared from the unsaturated butanol (IV) by catalytic hydrogenation in a solvent such as ethanol using palladium on charcoal as the catalyst. After filtration of the mixture and evaporation of the solvent, the product (VI) is obtained as a crystalline solid.

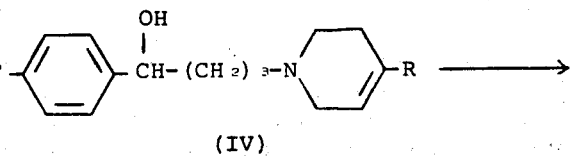

(IV)

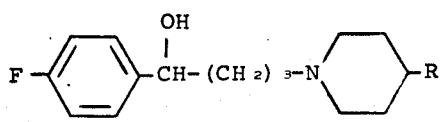

(VI)

In the fourth step, the unsaturated butanol (IV) is treated with stirring with a loweralkanoic anhydride such as acetic anhydride in the presence of a catalytic amount of a base such as pyridine, at 25°–30° C. for 18–24 hours. The mixture is evaporated to dryness at reduced pressure, and the residue is dissolved in ether and treated with a mineral acid such as hydrochloric acid to give the loweralkanoate ester as the mineral acid salt (VII).

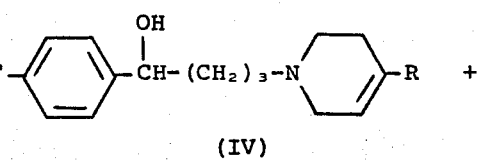

(IV)

(R'-CO)₂O →

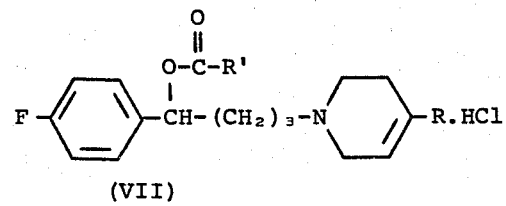

(VII)

The compounds of this invention will be more fully illustrated by the following specific examples wherein Examples 1–9 illustrate the preparation of the quaternary salts of this invention and Examples 10–26, the preparation of the central nervous system active butanols, butyrophenones and esters.

EXAMPLE 1

Preparation of 4-(5-Cyclopropyl-3-isoxazolyl)-1-(3-p-fluorobenzoylpropyl)pyridinium perchlorate A 1 g. portion of γ-chloro-p-fluorobutyrophenone and 0.9 g. of 4-(5-cyclopropyl-3-isoxazolyl)pyridine are heated in an oil bath overnight at 100° C. Ether is added to the solid mass with stirring. The ether is decanted and the solid is recrystallized from acetonitrile. This oily solid is dissolved in water and perchloric acid is added. The resulting tan precipitate is recrystallized sequentially from methanol, ethanol and ethanol, melting point 139°–141.5° C.

EXAMPLE 2

Preparation of 4-(3-Ethyl-5-pyrazolyl)-1-(3-p-fluorobenzoylpropyl)-pyridinium perchlorate A 2.0 g. portion of γ-chloro-p-fluorobutyrophenone and 1.7 g. of 4-(3-ethyl-5-pyrazolyl)pyridine are heated in an oil bath for 5 hours at 100° C. and then cooled overnight. The solid is slurried in ether several times and recrystallized from acetonitrile. This solid is dissolved in water and perchloric acid is added causing precipitation of a solid. This solid is recrystallized three times from methanol, m.p. 55°–75° C. (gas bubbles).

EXAMPLE 3

Preparation of 4-(5-Cyclopropyl-1,2,4-oxadiazol-3-yl)-1-[3-(p-fluorobenzoyl)-propyl]pyridinium perchlorate A 1.0 g. portion of γ-chloro-p-fluorobutyrophenone and 0.9 g. of 4-(5-cyclopropyl-1,2,4-oxadiazol-3-yl)pyridine are heated in an oil bath at 100° C. overnight. The resulting oil is slurried several times with ether. The oil is added to water and the mixture is stirred and filtered. Perchloric acid is added to the filtrate causing formation of a tan solid. This solid is washed with water and recrystallized twice from methanol, m.p. 183°–184° C.

EXAMPLE 4

Preparation of 1-(3-(p-Fluorobenzoylpropyl)-4-(4-methyl-2-thiazolyl)pyridinium chloride A 1.0 g. portion of γ-chloro-p-fluorobutyrophenone and 0.9 g. of 4-(4-methyl-2-thiazolyl)pyridine are heated in an oil bath at 95°–100° C. overnight. Ether is added and the mixture is filtered. The solid is recrystallized from acetonitrile. This solid is recrystallized from a mixture of alcohol and ether, m.p. 226°–228° C.

EXAMPLE 5

Preparation of 1-(3-p-Fluorobenzoylpropyl)-4-(3-methyl-5-isoxazolyl)pyridinium perchlorate A 2.0 g. portion of γ-chloro-p-fluorobutyrophenone and 1.6 g. of 4-(3-methyl-5-isoxazolyl)pyridine are heated in an oil bath overnight at 100° C. The mixture is slurried with ether several times. The solid is recrystallized from 100 ml. of acetonitrile. This solid is dissolved in water, filtered and perchloric acid is added to the filtrate. The resulting solid is recrystallized twice from methanol, m.p. 135°–136.5° C.

EXAMPLE 6

Preparation of 4-(5-Cyclopropyl-1,3,4-oxadiazol-2yl)-1-(3-p-fluorobenzoylpropyl)pyridinium perchlorate A 2.0 g. portion of γ-chloro-p-fluorobutyrophenone and 1.9 g. of 4-(5-cyclopropyl-1,3,4-oxadiazol-2-yl)pyridine are heated on a steam bath overnight. The mixture is slurried in ether and filtered. The resulting solid is recrystallized twice from ethanol. This solid is then recrystallized from acetonitrile yielding a solid (A). The filtrate on evaporation yields a solid (B) which is put on silica gel plates and extracted with methanol yielding a solid (C). Solids (A) and (C) are converted to the perchlorate, as previously described, combined and recrystallized from methanol, m.p. 168.5°–169° C.

EXAMPLE 7

Preparation of 1-(3-p-Fluorobenzoylpropyl)-3-(4-methyl-2-thiazolyl)-pyridinium perchlorate A 4.0 g. portion of γ-chloro-p-fluorobutyrophenone and 3.6 g. of 3-(4-methyl-2-thiazolyl)pyridine are heated on a steam bath overnight. The thick oil is slurried in ether several times until a tan solid is produced which is filtered and washed with ether. This solid is recrystallized from acetonitrile and then ethanol-ether, yielding a solid. The ethanol-ether mother liquor upon the addition of more ether yields an additional solid. The two solids are combined, converted to the perchlorate salt as previously described and recrystallized twice from methanol, m.p. 109°–110° C.

EXAMPLE 8

Preparation of 1-(3-p-Fluorobenzoylpropyl)-4-[5-(trifluoromethyl)-3-isoxazolyl]pyridinium perchlorate A 2.0 g. portion of γ-chloro-p-fluorobutyrophenone and 2.1 g. of 4-(5-trifluoromethyl-3-isoxazolyl)pyridine are heated on a steam bath overnight. The dark oil is slurried in ether several times and filtered. The brown solid is dissolved in water filtered and the filtrate is acidified with perchloric acid yielding a white solid. The solid is recrystallized twice from methanol, m.p. 64°–66° C.

EXAMPLE 9

Preparation of 1-(3-p-Fluorobenzoylpropyl)-4-(2-oxazolyl)-pyridinium perchlorate A 2.0 g. portion of γ-chloro-p-fluorobutyrophenone and 1.5 g. of 4-(2-oxazolyl)pyridine are heated on a steam bath overnight. The mixture is slurried in ether several times and filtered giving a dark solid which is recrystallized from acetonitrile, dissolved in water and filtered. The filtrate is acidified with perchloric acid, yielding a tan solid. This solid is recrystallized twice from methanol, m.p. 162°–163.5° C.

EXAMPLE 10

Preparation of
3,6-Dihydro-α-(p-fluorophenyl)-4-(3-methyl-5-isoxazolyl)pyridinebutanol To a 1.7 g. portion of 1-(3-p-fluorobenzoylpropyl)-4-(3-methyl-5-isoxazolyl)pyridinium perchlorate, prepared as described in Example 5, in 80 ml. of methanol is added 1.6 g. of sodium borohydride, portionwise with stirring. This mixture is stirred at room temperature for 2 hours. The mixture is evaporated to about one-half volume and poured into 150 ml. of cold water. The white solid which forms is recrystallized from aqueous ethanol, m.p. 116°–119° C.

EXAMPLE 11

Preparation of
4-(5-Cyclopropyl-1,2,4-oxadiazol-3-yl)-3,6--dihydro-α-(p-fluorophenyl)-1(2H)-pyridinebutanol To a 1.8 g. portion of 4-(5-cyclopropyl-1,2,4-oxadiazol-3-yl)-1-[3-(p-fluorobenzoyl)-propyl]-pyridinium perchlorate, prepared as described in Example 3, in 80 ml. of methanol is added, portionwise with stirring, 1.8 g. of sodium borohydride. The mixture is stirred for 2 hours and then poured into 300 ml. of cold water, causing a white solid to separate. This solid is collected and recrystallized from acetonitrile, m.p. 89°–92° C.

EXAMPLE 12

Preparation of
3,6-Dihydro-α-(p-fluorophenyl)-4-(4-methyl-2-thiazolyl)-1(2H)-pyridinebutanol To a 0.4 g. portion of 1-(3-p-fluorobenzoylpropyl)-4-(4-methyl-2-thiazolyl)pyridinium chloride, prepared as described in Example 4, in 20 ml. of methanol is added portionwise with stirring 0.4 g. of sodium borohydride. The mixture is stirred for 2 hours and then poured into water causing the formation of white solid which is separated and recrystallized from acetone and water, m.p. 89°–90.5° C.

EXAMPLE 13

Preparation of
3,6-Dihydro-4-(3-ethyl-5-pyrazolyl)-α-(p-fluorophenyl)-1(2H)-pyridinebutanol To a 2.2 g. portion of 4-(3-ethyl-5-pyrazolyl)-1-(3-p-fluorobenzoylpropyl)pyridinium perchlorate, prepared as described in Example 2, in 100 ml. of methanol is added portionwise with stirring 2.2 g. of sodium borohydride. The mixture is stirred for 2 hours and then poured into ice water causing formation of a white solid which was collected and recrystallized from methanol, m.p. 140.5°–141.5° C.

EXAMPLE 14

Preparation of
3,6-Dihydro-α-(p-fluorophenyl)-4-[5-(trifluoromethyl)-3-isoxazolyl]-1(2H)-pyridinebutanol To a 1.0 g. of 1-(3-p-fluorobenzoylpropyl)-4-[5-(trifluoromethyl)-3-isoxazdyl]pyridinium perchlorate, prepared as described in Example 8, in 40 ml. of methanol, is added portionwise with stirring 1.0 g. of sodium borohydride. The mixture is stirred for 2 hours and poured into ice-water causing the formation of a white solid which is collected and recrystallized from methanol, m.p. 120.5°–121.5° C.

EXAMPLE 15

Preparation of
3,6-Dihydro-α-(p-fluorophenyl)-4-(2-oxazolyl)-1(2H)-pyridinebutanol To a 1.75 g. portion of 1-(3-p-fluorobenzoylpropyl)-4-(2-oxazolyl)pyridinium perchlorate, prepared as described in Example 9, in 75 ml. of methanol, is added portionwise with stirring 1.75 g. of sodium borohydride. The mixture is stirred for 1 ½ hours, allowed to stand, some of the methanol is evaporated and the mixture is poured into ice water causing the formation of a tan solid which is recovered by filtration, m.p. 100°–103° C.

EXAMPLE 16

Preparation of
α-(p-Fluorophenyl)-4-(4-methyl-2-thiazolyl)-1-piperidinebutanol

A 0.35 g. portion of 3,6-dihydro-α-(p-fluorophenyl)-4-(4-methyl-2-thiazolyl)-1(2H)-pyridinebutanol, prepared as described in Example 12, is dissolved in 10 ml. of ethanol and 0.1 g. of palladium on carbon catalyst is added. The mixture is reduced to room temperature and pressure for about 26 hours. The mixture is filtered and the filtrate evaporated yielding a white solid which is recrystallized from acetonitrile giving a white crystalline solid, m.p. 98°–99° C.

EXAMPLE 17

Preparation of α-(p-Fluorophenyl)-4-(2-oxazolyl)-1-piperidinebutanol

A 0.32 g. portion of 3,6-dihydro-α-(p-fluorophenyl)-4-(2-oxazolyl)-1(2H)-pyridinebutanol, prepared as described in Example 15, is dissolved in 10 ml. of ethanol and 0.1 g. of palladium on carbon catalyst is added. The mixture is reduced at room temperature and pressure and for 4 hours and then filtered. The filtrate is evaporated giving an oil which solidifies to a white solid. This solid is recrystallized twice from acetonitrile, m.p. 99°–100° C.

EXAMPLE 18

Preparation of
3,6-Dihydro-4-(3-methyl-5-isoxazolyl)-α-phenyl-1(2H)-pyridinebutanol To a 4.1 g. portion of 1-(3-benzoylpropyl)-4-(3-methyl-5-isoxazolyl)pyridinium perchlorate [prepared by the reaction of γ-chlorobutyrophenone and 4-(3-methyl-5-isoxazolyl)pyridine as described in the previous examples] in 200 ml. of methanol is added, portionwise with stirring, 4.1 g. of sodium borohydride. The mixture is allowed to stand at room temperature overnight, evaporated to about one-half volume and poured into ice water. The white solid is collected and recrystallized from acetonitrile, m.p. 108°–109° C.

EXAMPLE 19

Preparation of
4-[3,6-Dihydro-4-(3-methyl-5-isoxazolyl)-1(2H)-pyridyl]-4'-fluoro-butyrophenone A 1.65 g. portion of 3,6-dihydro-α-(p-fluorophenyl)-4-(3-methyl-5-isoxazolyl)-1(2H)-pyridine butanol, prepared as described in Example 10, in 35 ml. of acetic acid is stirred at room temperature. A 30 ml. portion of chromic acid in acetic acid (prepared by dissolving 1.1 gm. of chromium oxide in 50 ml. of acetic acid and 10 ml. of water) is added dropwise and the mixture is stirred for 3 hours and then allowed to stand overnight. A few drops of methanol are added and sufficient solid sodium bicarbonate to neutralize the solution. Water is also added. The mixture is extracted 3 times with ether. The extracts are dried over magnesium sulfate, filtered and evaporated yielding a pink solid which is recrystallized twice from methanol, m.p. 96°–98° C.

EXAMPLE 20

Preparation of
4-[4-(5-Cyclopropyl-1,2,4-oxadiazol-3-yl)-3,6-dihydro-1(2H)-pyridyl]-4'-fluoro-butyrophenone A 0.36 g. portion of 4-(5-cyclopropyl-1,2,4-oxadiazol-3-yl)-3,6-dihydro-α-(p-fluorophenyl)-1(2H)-pyridinebutanol, prepared as described in Example 11, in 10 ml. of acetic acid is stirred at room temperature. A 6 ml. portion of chromic acid in acetic acid solution is added dropwise. The mixture is stirred for 2 hours and then allowed to stand overnight. A few drops of methanol and some water is added and the solution is neutralized with solid sodium bicarbonate. The mixture is extracted 3 times with ether. The extracts are dried over magnesium sulfate, filtered and evaporated, yielding a white solid which is recrystallized from aqueous methanol, m.p. 67°–68° C.

EXAMPLE 21

Preparation of
4-[3,6-Dihydro-4-(4-methyl-2-thiazolyl)-1(2H)-pyridyl]-4'-fluoro-butyrophenone A 1.4 g. portion of 3,6-dihydro-α-(p-fluorophenyl)-4-(4-methyl-2-thiazolyl)-1(2H)-pyridinebutanol, prepared as described in Example 12, in 30 ml. of acetic acid is stirred at room temperature. A 24 ml. portion of chromic acid in acetic acid is added dropwise. The mixture is stirred for 3 hours and then allowed to stand overnight. The mixture is poured onto ice water and neutralized with sodium carbonate. The mixture is extracted 3 times with ether. The extracts are dried over magnesium sulfate, filtered and evaporated, giving an oil which solidifies. This solid is recrystallized twice from aqueous methanol yielding a tan solid, m.p. 81°–82° C.

EXAMPLE 22

Preparation of
4-(3,6-Dihydro-4-isoxazolyl-1(2H)-pyridyl)-4'-fluoro-butyrophenone A 1.58 g. portion of 3,6-dihydro-α-(p-fluorophenyl)-4-(2-oxazolyl)-1(2H)-pyridinebutanol, prepared as described in Example 15, in 45 ml. of acetic acid is stirred at room temperature. A 30 ml. portion of chromic acid in acetic acid is added dropwise. The mixture is stirred for 2 hours and allowed to stand overnight. A few drops of methanol are added, the mixture is poured into ice water and neutralized with sodium carbonate. The mixture is extracted with ether. The ether extract is dried over magnesium sulfate, filtered and evaporated yielding an oil which solidifies. This solid is dissolved in ether, alcoholic HCl is added and the mixture is filtered. The solid is slurried in acetone, filtered and recrystallized twice from ethanol, m.p. 178°–178.5° C.

EXAMPLE 23

Preparation of
3,6-Dihydro-α-(p-fluorophenyl)-4-(3-methyl-5-isoxazolyl)-1(2H)-pyridinebutanol acetate, hydrochloride A one gram portion of 3,6-dihydro-α-(p-fluorophenyl)-4-(3-methyl-5-isoxazolyl)-1(2H)-pyridinebutanol prepared as described in Example 10, in 6 ml. of acetic anhydride and 2 drops of pyridine is stirred at room temperature for about 1 hour. The clear solution, after standing for 18–20 hours is evaporated to dryness. The residue is dissolved in ether and treated with 2.5N alcoholic hydrogen chloride solution to give a white solid. One recrystallization from methanol-ether gives a white crystalline solid, m.p. 156.5°–157° C dec.

EXAMPLE 24

Preparation of
3,6-Dihydro-α-(p-fluorophenyl)-4-(3-methyl-5-isoxazolyl)-1(2H)-pyridinebutanol propionate, hydrochloride A one gram portion of 3,6-dihydro-α-(p-fluorophenyl)-4-(3-methyl-5-isoxazolyl)-1(2H)-pyridinebutanol prepared as described in Example 10, is treated with 6 ml. of propionic anhydride and pyridine in the same manner as described in Example 23. The product is obtained as a white crystalline solid, m.p. 164.5°–165.5° C. dec.

EXAMPLE 25

Preparation of
3,4-Dihydro-α-(p-fluorophenyl)-4-(2-Oxazolyl)-1(2H)-pyridinebutanol acetate, hydrochloride A 1.3 g. portion of 3,6-dihydro-α-(p-fluorophenyl)-4-(2-oxazolyl)-1(2H)-pyridinebutanol, prepared as described in Example 15, in 8 ml. of acetic anhydride and 2 drops of pyridine is stirred at room temperature for 18–20 hours and then evaporated to dryness. The residue is dissolved in ether and treated with 2.5N alcoholic hydrogen chloride solution. The solid which separates is recrystallized from methanol-ether to give a white crystalline solid, m.p. 176°–176.5° C.

EXAMPLE 26

Preparation of
3,4-Dihydro-α-(p-fluorophenyl)-4-(2-oxazolyl)-1(2H)-pyridinebutanol propionate, hydrochloride A mixture of 2.6 g. of 3,6-dihydro-α-(p-fluorophenyl)-4-(2-oxazolyl)-1(2H)-pyridinebutanol, prepared as described in Example 15, 16 ml. of propionic anhydride and 2 drops of pyridine is stirred at room temperature for 18–20 hours and then evaporated to dryness. The residue is dissolved in ether and treated with 2.5N alcoholic hydrogen chloride. The sticky solid which separates is recrystallized from isopropyl alcohol to give a white crystalline solid, m.p. 164°–165° C.

We claim:

1. A compound of the formula:

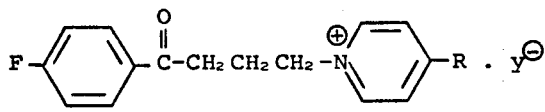

wherein R is

,

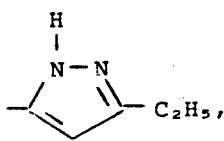   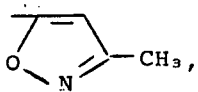,

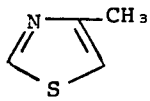,

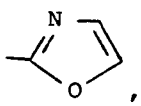   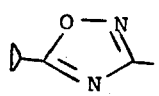

and

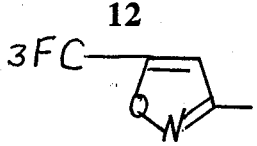

and y is an anion of a non-toxic inorganic halogen acid.

2. A compound according to claim 1, 4-(5-cyclopropyl-3-isoxazolyl)-1-(3-p-fluorobenzoylpropyl)-pyridinium perchlorate.

3. A compound according to claim 1, 4-(3-ethyl-5-pyrazolyl)-1-(3-p-fluorobenzoylpropyl)pyridinium perchlorate.

4. A compound according to claim 1, 4-(5-cyclopropyl-1,2,4-oxadiazol-3-yl)-1-[3-(p-fluorobenzoyl)-propyl]pyridinium perchlorate.

5. A compound according to claim 1, 1-(3-p-fluorobenzoylpropyl)-4-(4-methyl-2-thiazolyl)-pyridinium chloride.

6. A compound according to claim 1, 1-(3-p-fluorobenzoylpropyl)-4-(3-methyl-5-isoxazolyl)-pyridinium perchlorate.

7. A compound according to claim 1, 4-(5-cyclopropyl-1,2,4-oxadiazol-2-yl)-1-(3-p-fluorobenzoylpropyl)-pyridinium perchlorate.

8. A compound according to claim 1, 1-(3-p-fluorobenzoylpropyl)-3-(4-methyl-2-thiazolyl)-pyridinium perchlorate.

9. A compound according to claim 1, 1-(3-p-fluorobenzoylpropyl)-4-[5-(trifluoromethyl)-3-isoxazolyl]pyridinium perchlorate.

10. A compound according to claim 1, 1-(3-p-fluorobenzoylpropyl)-4-(2-oxazolyl)pyridinium perchlorate.

* * * * *